United States Patent [19]

Sugimoto et al.

[11] Patent Number: 4,493,837

[45] Date of Patent: Jan. 15, 1985

[54] THEOBROMINE DERIVATIVES

[75] Inventors: Hachiro Sugimoto, Noda; Sachiyuki Hamano, Tokyo; Tadao Shoji, Kagamihara; Takeru Kaneko, Hatogaya; Takeshi Uzuo, Shiki, all of Japan

[73] Assignee: Eisai Co., Ltd., Tokyo, Japan

[21] Appl. No.: 435,518

[22] Filed: Oct. 20, 1982

Related U.S. Application Data

[63] Continuation of Ser. No. 126,616, Mar. 3, 1980, abandoned.

[30] Foreign Application Priority Data

Mar. 5, 1979 [JP] Japan ............................... 54-24570

[51] Int. Cl.$^3$ .................. C07D 473/10; A61K 31/52

[52] U.S. Cl. .................................. 424/253; 544/267; 544/268; 544/269

[58] Field of Search ............... 544/267, 268, 269; 424/253

[56] References Cited

U.S. PATENT DOCUMENTS 3,459,753 7/1969 Boltze et al. ..................... 424/253
3,996,361 12/1976 Friebe et al. ..................... 424/253

Primary Examiner—Nicholas S. Rizzo
Attorney, Agent, or Firm—Flynn, Thiel, Boutell & Tanis

[57] ABSTRACT

There are disclosed theobromine derivatives wherein theobromine is substituted at the 1 position with substituted piperazino, homopiperazino and piperidino groups, and pharmacologically acceptable acid addition salts thereof. The compounds exhibit vasodilating and psychotropic and analgesic activities.

18 Claims, No Drawings

THEOBROMINE DERIVATIVES

This is a continuation of application Ser. No. 126,616 filed Mar. 3, 1980 now abandoned.

This invention relates to theobromine derivatives having excellent activities as medicines and to a process for producing said derivatives.

More particularly, the present invention relates to theobromine derivatives expressed by the following general formula

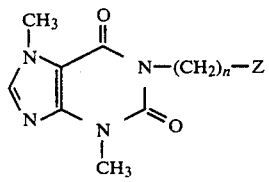   [I]

wherein Z is a member selected from the following groups;

A. a group expressed by the formula

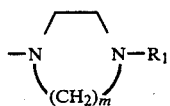

wherein m is the integer 2 or 3, and $R_1$ is pyridyl or a group expressed by the formula

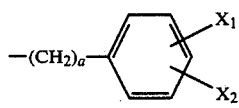

wherein $X_1$ and $X_2$, which can be the same or different, each is hydrogen, lower alkyl, lower alkoxy, trifluoromethyl or halogen, and a is an integer of 0 to 3;

B. a group expressed by the formula

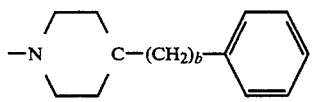

wherein b is an integer of 0 to 3;

C. a group expressed by the formula

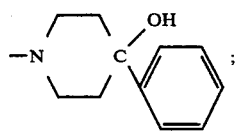

D. a group expressed by the formula

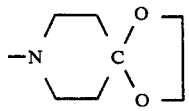

and E. a group expressed by the formula

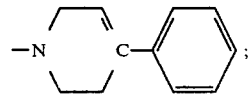

and wherein n is an integer of 2 to 8, with the proviso that n is an integer of 3 to 8 when Z is

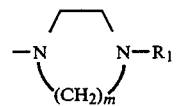

in which m is 2 and $R_1$ is

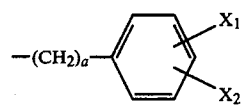

if a is 0 and both $X_1$ and $X_2$ are both hydrogen. The present invention also relates to a process for preparing the abovementioned theobromine derivatives.

In the abovementioned general formula [I], the lower alkyl group and the lower alkoxy group in the definition of $X_1$ and $X_2$ for $R_1$ represents $C_1$ to $C_6$ straight chain or branched chain alkyl groups, e.g., methyl, ethyl, n-propyl, isopropyl, isobutyl, 1-methylpropyl, tert-butyl, n-pentyl, 1-ethylpropyl, isoamyl and n-hexyl, and corresponding alkoxy groups ($C_1$ to $C_6$) based on these alkyl groups. The term "halogen" represents chlorine, bromine, iodine and fluorine.

The compounds of the formula [I], in accordance with the present invention, can easily be converted to acid addition salts by reacting them with pharmaceutically acceptable organic or inorganic acids. Examples of such inorganic acids include hydrochloric acid, hydrobromic acid, hydriodic acid and sulfuric acid, and examples of such organic acids include maleic acid, fumaric acid, succinic acid, acetic acid, malonic acid, citric acid and benzoic acid.

The theobromine derivatives of formula [I], according to the present invention, are all novel compounds that have not heretofore been disclosed, and they are compounds having low toxicity and a remarkable vasodilating action. In other words, the compounds of the present invention improve not only the peripheral blood flow, but also remarkably improve the blood flow in the brain and the coronary artery. Accordingly, the compounds of the present invention are effective as medicines for treating various diseases arising from the perfusion of peripheral blood flow and for improving the insufficiency of cerebral blood vessels and their sequela, and also for treating angina pectoris, myocardial infarction and so forth. The theobromine derivatives provided by the present invention have excellent action on the central nervous system so that they can also be used as psychotropic (neuroleptic, anti-anxiety) drug. Moreover, these derivatives also have excellent analgesic action so that they can also be used as analgesic agent.

The compounds of formula [I] of the present invention can be prepared by various methods. Among them, the reaction scheme of a suitable method is illustrated below:

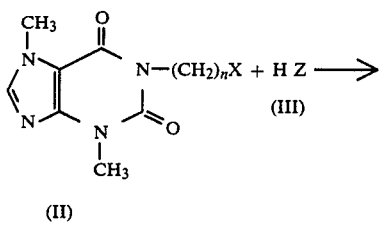

wherein X is a halogen atom or a p-toluenesulfonyloxy group, and each of Z and n has the same meaning as previously defined.

In other words, the compounds [I] of the present invention can be obtained by reacting the compound expressed by the general formula [II] with the compound expressed by the general formula [III]. A definite example in the case where Z is a group expressed by the following formula

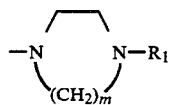

is given below:

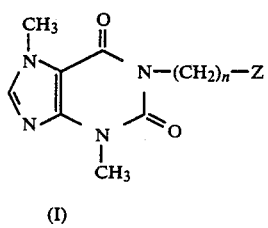

The reaction of the present invention can be carried out in the absence of a solvent. Alternatively, it can be carried out in the presence of a solvent selected suitably from those solvents which do not participate in the reaction. Examples of such solvents are lower alcohol-type solvents, e.g., methanol, ethanol, propanol, isopropanol, etc., benzene type solvents, e.g., benzene, toluene, xylene, etc., and ether-type solvents, e.g., diethyl ether, tetrahydrofuran, etc. Although the reaction proceeds at room temperature, it is preferred to heat up the reaction mixture to the boiling point of the solvent used. The progress of the reaction can be made smoother by adding to the reaction system such acid-trapping agents as triethylamine, alkali metal bicarbonate, alkali metal carbonate, pyridine and so forth.

Next, the excellent pharmacological action of the compounds of the present invention will be explained with reference to typical compounds thereof.

1. Blood flow-increasing action

The blood flow at a femoral artery is measured by each of four male and female mongrel dogs weighing from 10 to 14 kg. That is, each subject is anesthetized by injecting intravenously 30 mg/kg of pentobarbital and one side femoral artery is exposed. A probe (2.5 mm diameter) of a magnetic blood flow meter (Model MF-26, a product of Nihon-Koden K.K.) is fitted to this artery and a catheter is inserted into and fixed to a side branch of this femoral artery. Intraarterial injection of 0.1 ml of the sample is then made and the average blood flow is measured. The dose of the sample is 0.03 mg/kg. When the blood flow-increasing action is strong, the dose is made 0.003 mg/kg and when the blood flow-increasing action is even stronger, it is made 0.0003 mg/kg in order to conduct the experiments. Papaverine is used as a control medicine, and comparison is made between it and the compounds of the present invention, with the results being set forth in Table 1. The numerical values in Table 1 represent the relative values of the compounds of this invention when the height of the blood flow-increase curve obtained by administration of 0.03 mg/kg papaverine is arbitrarily assigned the value 1.00. In other words, these values represent the ratio of the efficacy of the compounds of this invention relative to the activity of papaverine, with the latter being assigned the value 1.

TABLE 1

| Compound | Specific activity |
|---|---|
| Control | |
| Papaverine | 1 |
| Compound of this Invention | |

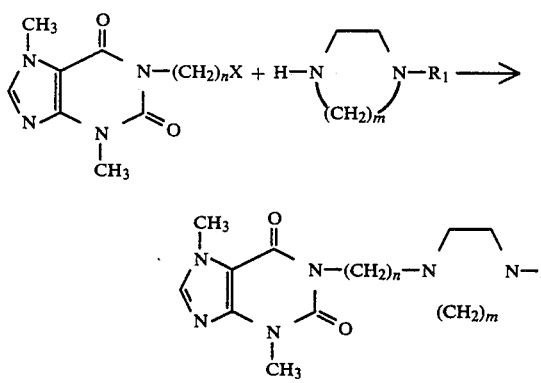

TABLE 1-continued

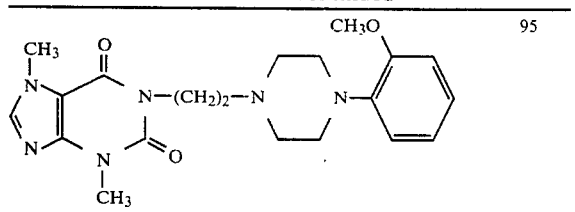

95

It is evident from Table 1 that the compounds of the present invention exhibit extremely excellent blood flow-increasing actions and are effective as blood flow-improving agents.

2. Psychotropic Action (1) Inhibition of grooming behavior in mice;

The grooming behavior-inhibiting action of the compounds of the present invention was examined by the following experiments, using the method disclosed in O. Rohte; Psychopharmacologia, Vol. 14, 18–22 (1969).

When mice are applied oily ink to their back fur near the base of the tail, they exhibit grooming behavior, such as licking and/or plucking of the painted region. In this experiment, each sample (the compounds of the present invention, and chlorpromazine and diazepam as control medicines) was prepared in a form of 5% arabic gum suspension of 0.1 ml/10 g body weight of the animal.

Forty minutes after oral administration of each sample, the oily ink was painted on each mouse. And 10 minutes later, the number of grooming responses was counted for a 20-minutes period. A 5% arabic gum solution alone was administered to the control group.

The results are shown in Table 2-1.

TABLE 2-1

| Compound | | dose (mg/kg) P.O. | Number of mice | Number of Grooming responses | % Inhibition |
|---|---|---|---|---|---|
| Control Group | 5% arabic gum | | 40 | 30.1 ± 3.5 | — |
| Control medicine | chlorpromazine | 0.625 | 10 | 21.4 ± 4.3 | 30 |
| | | 2.5 | 10 | 2.9 ± 2.9 | 91 |
| | | 10 | 10 | 5.8 ± 5.8 | 61 |
| | | 40 | 10 | 5.9 ± 5.9 | 80 |
| | diazepam | 0.625 | 10 | 14.3 ± 4.2 | 53 |
| | | 2.5 | 10 | 9.5 ± 5.2 | 68 |
| | | 10 | 10 | 7.6 ± 3.2 | 75 |
| Compound of this Invention | (structure with $CF_3$) | 0.625 | 10 | 15.5 ± 5.8 | 49 |
| | | 2.5 | 10 | 16.5 ± 5.9 | 46 |
| | | 10 | 10 | 1.6 ± 1.6 | 95 |
| | | 40 | 10 | 0 | 100 |
| | (structure with $OCH_3$) | 0.625 | 10 | 23.4 ± 6.1 | 23 |
| | | 2.5 | 10 | 15.6 ± 4.5 | 49 |
| | | 10 | 10 | 9.5 ± 4.1 | 68 |
| | | 40 | 10 | 0 | 100 |

It is evident from Table 2-1 that the compounds of the present invention have a grooming behavior-inhibiting action substantially equal or superior to that of chlorpromazine and diazepam.

(2) Inhibition of the fighting behavior in mice;

The anti-fighting action was examined in the following experiment, using the method disclosed in Ralph E. Tedeshi et al, Journal of Pharmacology and Experimental Therapeutics, Vol. 125, 28–34 (1959).

A pair of mice was placed in a plastic cage (16×10×18 cm) with the grid floor and applied electrical shocks (3 mA, 5 Hz, 50 msec.) during a 3-minutes period to their feet to induce the fighting behavior between the mice.

In this experiment, each sample (the compounds of the present invention, and chlorpromazine and diazepam as control medicines) was prepared in a form of a 5% arabic gum suspension and was orally administered to the mice. One hour after oral administration, the fighting behavior was observed. A 5% arabic gum solution was administered to the control group. Ten pairs of mice were used for each dose level.

The results are shown in Table 2-2.

TABLE 2-2

| | Compound | dose (mg/kg) P.O. | No. of experiments | No. of fighting episodes | % Inhibition |
|---|---|---|---|---|---|
| Control Group | 5% arabic gum | | 10 | 5.6 ± 0.5 | — |
| Control Medicines | chlorpromazine | 0.625 | 10 | 3.9 ± 0.8 | 30 |
| | | 2.5 | 10 | 3.1 ± 1.0 | 45 |
| | diazepam | 0.625 | 10 | 4.0 ± 1.0 | 29 |
| | | 1.25 | 10 | 2.1 ± 0.9 | 63 |
| Compounds of this invention | 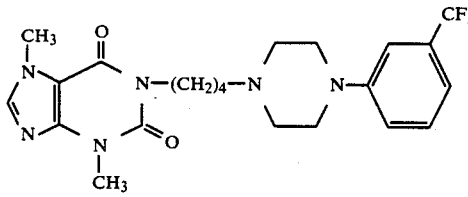 | 0.625 | 10 | 4.2 ± 0.7 | 25 |
| | | 2.5 | 10 | 1.0 ± 0.2 | 81 |
| | 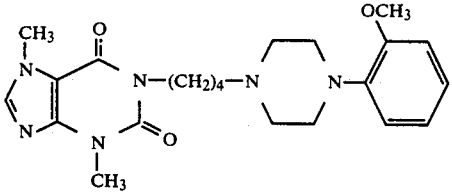 | 0.625 | 10 | 3.3 ± 0.7 | 41 |
| | | 2.5 | 10 | 1.6 ± 0.4 | 71 |

It is evident from Table 2-2 that the compounds of the present invention exhibit a more potent fighting behavior-inhibiting action (anti-fighting action) than chlorpromazine and diazepam.

It is also evident the foregoing Tables 2-1 and 2-2 that the compounds of the present invention have a potent psychotropic action and are useful as neuroleptic or anti-anxiety drug.

3. Analgesic action

Anti-writhing activity in mice;

The analgesic action of the compounds of the present invention was examined by the following experiment, using the writhing method disclosed in E. Siegmund et al; Proc. Soc. Exp. Biol. & Med., Vol. 95, 729 (1957).

Thirty minutes after subcutaneous injection of the compounds of the present invention, 2 mg/kg of phenylquinone was injected intraperitoneally to the mice. And 5 minutes later, the total number of writhes was counted for 4 minutes. Four mice were used for each dose level. The results are shown in Table 3.

It is evident from Table 3 that the compounds of the present invention exhibit the potent analgesic activity and useful as the analgesic agents.

TABLE 3

| Compound | Dose (mg/kg) s.c. | No. of mice | % Inhibition |
|---|---|---|---|
| 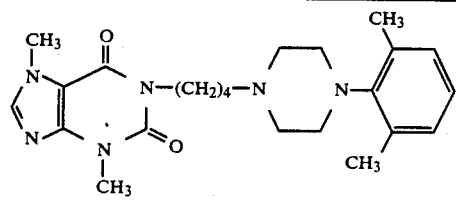 | 2.5 | 4 | 0 |
| | 5.0 | 4 | 53 |
| | 10.0 | 4 | 77 |
| | 25.0 | 4 | 85 |
| 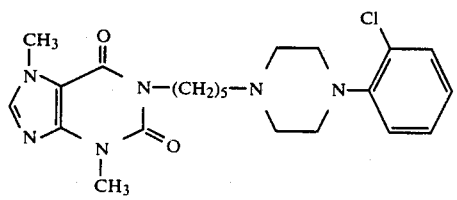 | 1.0 | 4 | 0 |
| | 2.5 | 4 | 56 |
| | 5.0 | 4 | 87 |
| | 10.0 | 4 | 100 |

TABLE 3-continued

| Compound | Dose (mg/kg) s.c. | No. of mice | % Inhibition |
|---|---|---|---|
| [structure: CH3-N-imidazole-C(=O)-N-(CH2)6-N-piperazine-N-(2-Cl-phenyl), with N-CH3 and C=O on other ring] | 0.25 | 4 | 10 |
| | 0.5 | 4 | 70 |
| | 1.0 | 4 | 80 |
| | 2.5 | 4 | 90 |
| | 5.0 | 4 | 100 |

The compounds of this invention are useful in the form of pharmaceutical compositions suitable for oral or parenteral use. Essentially, they comprise a pharmacologically effective amount of one of the compounds of this invention in admixture with a pharmaceutically acceptable, organic or inorganic, solid or liquid carrier, which usually represents the major portion by weight of such composition. These preparation are in solid form, for example, as capsules, tablets or dragees, in liquid form, for example, as solutions or suspensions.

The following examples will further illustrate the present invention. However, the invention is not limited to these examples.

EXAMPLE 1

Preparation of 1-{2-[4-p-methoxyphenylpiperazinyl-(1)]ethyl}-theobromine

A mixture of 6.9 g of 1-(2-bromoethyl)theobromine, 3.8 g of p-methoxyphenylpiperazine and 4.0 g of triethylamine is stirred under reflux in benzene. The hydrochloride salt of triethylamine is removed by filtration and the filtrate is extracted with dilute hydrochloric acid. After being rendered alkaline with dilute sodium hydroxide, the resulting extract is again extracted with chloroform. After the chloroform layer is washed with water, the reaction product is dried with anhydrous potassium carbonate. The solvent is removed by distillation. The resulting crude crystals are recrystallized from methanol to give 4.9 g (61.3% yield) of the title compound 1-{2-[4-p-methoxyphenylpiperazinyl-(1)]ethyl}theobromine.

M.P.: 157°–159° C.

Elementary analysis calculated for $C_{20}H_{26}O_3N_6$

| | C | H | N |
|---|---|---|---|
| Calculated (%): | 60.27 | 6.59 | 21.09 |
| Found (%): | 60.46 | 6.43 | 21.15 |

EXAMPLE 2

Preparation of 1-{3-[4-o-methylphenylpiperazinyl-(1)]-n-propyl}theobromine

A mixture of 7.2 g of 1-(3-bromo-n-propyl)theobromine, 3.5 g of o-methylphenylpiperazine and 4.0 g of triethylamine is stirred for 16 hours under reflux in benzene. The resulting crude crystals obtained as a result of the same procedures as described in Example 1 are recrystallized from ethanol to give 6.3 g (91.3% yield) of the title compound 1-{3-[4-o-methylphenylpiperazinyl-(1)]-n-propyl}theobromine.

M.P.: 152°–154° C.

Elementary analysis calculated for $C_{21}H_{28}O_2N_6$

| | C | H | N |
|---|---|---|---|
| Calculated (%): | 63.60 | 7.13 | 21.20 |
| Found (%): | 63.40 | 7.20 | 21.31 |

EXAMPLE 3

Preparation of 1-{4-[4-chlorobenzylhomopiperazinyl-(1)]-n-butyl}theobromine

A mixture of 7.5 g of 1-(4-bromo-n-butyl)theobromine, 4.5 g of p-chlorobenzylhomopiperazine and 4.0 g of triethylamine is stirred under reflux in benzene as solvent. Thereafter, the reaction product is treated in the same way as described in Example 1. The resulting oily matter is mixed with isopropyl ether, is left standing while being cooled with ice and is allowed to crystallize. The resulting crude crystals are recrystallized from ethanol to give 5.8 g (67.5%) of the title compound 1-{4-[4-p-chlorobenzylhomopiperazinyl-(1)]-n-butyl}theobromine.

M.P.: 71°–73° C.

Elementary analysis calculated for $C_{23}H_{31}O_2N_6Cl$

| | C | H | N |
|---|---|---|---|
| Calculated (%): | 60.17 | 6.82 | 18.31 |
| Found (%): | 59.94 | 6.86 | 18.43 |

EXAMPLE 4

Preparation of 1-{5-[4-piperidoneethyleneketal)-yl-(1)]-n-pentyl}theobromine A mixture of 7.9 g of 1-(5-bromo-n-pentyl)theobromine, 3.5 g of 4-piperidoneethyleneketal and 4.0 g of triethylamine is stirred under reflux in benzene. The reaction product is then washed with water and is dried with anhydrous potassium carbonate. The solvent is removed by distillation. The resulting crude crystals are recrystallized from acetoneisopropyl ether to give 5.3 g (69.0%) of the title compound 1-{5-[4-piperidoneethyleneketal)-yl-(1)]-n-pentyl}theobromine.

M.P.: 95°–96° C.

Elementary analysis calculated for $C_{19}H_{29}O_4N_5$

|  | C | H | N |
|---|---|---|---|
| Calculated (%): | 58.29 | 7.48 | 17.88 |
| Found (%): | 58.06 | 7.54 | 18.02 |

EXAMPLES 5-77

Examples 5 through 77 provide the compounds illustrated in Tables 4-1 to 4-8 in accordance with the method of Example 1.

TABLE 4

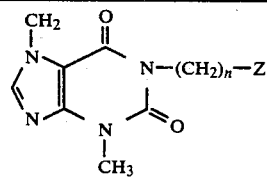

| Example No. | n | Z | M.P. (C) | Molecular formula | Elementary analysis upper column: Calculated lower column: Found | | |
|---|---|---|---|---|---|---|---|
| | | | | | C | H | N |
| 5 | 2 | ―N⟨piperazine⟩N―(2-OCH₃-phenyl) | 164–166 | $C_{20}H_{26}O_3N_6$ | 60.27 / 60.45 | 6.59 / 6.53 | 21.09 / 20.97 |
| 6 | 2 | ―N⟨piperazine⟩N―(3-OCH₃-phenyl) | 145–146 | $C_{20}H_{26}O_3N_6$ | 60.27 / 60.33 | 6.59 / 6.66 | 21.09 / 21.10 |
| 7 | 2 | ―N⟨piperazine⟩N―(2-CH₃-phenyl) | 115–117 | $C_{20}H_{26}O_2N_6$ | 62.79 / 62.63 | 6.87 / 7.04 | 21.98 / 21.83 |
| 8 | 2 | ―N⟨piperazine⟩N―(4-Cl-phenyl) | 199–200 | $C_{19}H_{23}O_2N_6Cl$ | 56.63 / 56.61 | 5.77 / 5.79 | 20.86 / 20.83 |
| 9 | 2 | ―N⟨piperazine⟩N―(3-Cl-phenyl) | 171–172 | $C_{19}H_{23}O_2N_6Cl$ | 56.63 / 56.80 | 5.77 / 5.61 | 20.86 / 20.90 |
| 10 | 2 | ―N⟨piperazine⟩N―(4-F-phenyl) | 183–185 | $C_{19}H_{23}O_2N_6F$ | 59.04 / 58.93 | 6.01 / 5.97 | 21.75 / 21.67 |
| 11 | 2 | ―N⟨piperazine⟩N―(3-CF₃-phenyl) | 156–158 | $C_{20}H_{23}O_2N_6F_3 \cdot \frac{1}{2}H_2O$ | 53.92 / 53.57 | 5.21 / 5.26 | 18.87 / 19.03 |

TABLE 4-continued

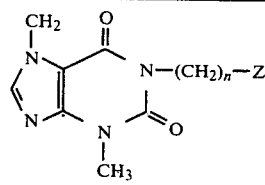

| Example No. | n | Z | M.P. (°C) | Molecular formula | Elementary analysis upper column: Calculated lower column: Found | | |
|---|---|---|---|---|---|---|---|
| | | | | | C | H | N |
| 12 | 2 | −N⌇N−(2-pyridyl) | 141–142 | C₁₈H₂₃O₂N₇ ·½H₂O | 57.12 57.78 | 6.40 6.45 | 25.91 26.19 |
| 13 | 2 | −N⌇N−phenyl | 136–137 | C₂₀H₂₆O₂N₆ | 62.79 62.95 | 6.87 7.19 | 21.98 22.22 |
| 14 | 2 | −N⌇N−CH₂−(2-Cl-phenyl) | 257–258 (dec.) | C₂₁H₂₇O₂N₆Cl ·2HCl | 50.05 49.74 | 5.81 5.70 | 16.69 16.81 |
| 15 | 2 | −N⌇N−CH₂−phenyl | 127–128 | C₁₀H₂₆O₂N₆ | 62.79 63.17 | 6.87 6.92 | 21.98 21.82 |
| 16 | 2 | −N⌇-phenyl | 140–142 | C₂₀H₂₅O₂N₅ | 65.36 65.72 | 6.87 6.88 | 19.06 19.32 |
| 17 | 2 | −N⌇-C(OH)(phenyl) | 197–199 | C₂₀H₂₅N₅O₃ | 62.63 62.71 | 6.58 6.61 | 18.27 18.21 |
| 18 | 2 | −N⌇-CH₂-phenyl | 197–198 | C₂₁H₂₇O₂N₅ | 66.10 66.45 | 7.15 7.48 | 18.36 18.55 |
| 19 | 2 | −N⌇-(CH₂)₃-phenyl | 94–95 | C₂₃H₃₁N₅O₂ | 67.44 67.98 | 7.64 7.75 | 17.10 17.29 |
| 20 | 3 | −N⌇N−phenyl | 142–144 | C₂₀H₂₅O₂N₅ | 62.79 62.86 | 6.87 6.93 | 21.98 22.17 |
| 21 | 3 | −N⌇N−(2-OCH₃-phenyl) | 180–182 | C₂₁H₂₈O₃N₆ | 61.13 61.05 | 6.85 6.72 | 20.38 20.41 |

TABLE 4-continued
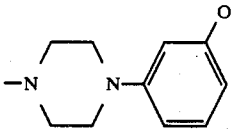
| Example No. | n | Z | M.P. (°C) | Molecular formula | Elementary analysis upper column: Calculated lower column: Found | | |
|---|---|---|---|---|---|---|---|
| | | | | | C | H | N |
| 22 | 3 | 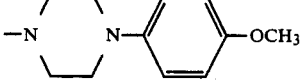 | 94–96 | $C_{21}H_{28}O_3N_6$ | 61.13<br>61.00 | 6.85<br>6.93 | 20.38<br>20.35 |
| 23 | 3 | 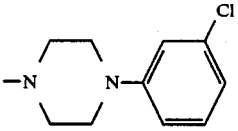 | 164–167 | $C_{21}H_{28}O_3N_6$ | 61.13<br>61.35 | 6.85<br>6.67 | 20.38<br>20.67 |
| 24 | 3 | 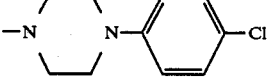 | 151–152 | $C_{20}H_{25}O_2N_6Cl$ | 57.60<br>57.84 | 6.05<br>6.17 | 20.16<br>20.25 |
| 25 | 3 | 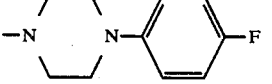 | 165–167 | $C_{20}H_{25}O_2N_6Cl$ | 57.58<br>57.63 | 6.06<br>6.08 | 20.17<br>20.21 |
| 26 | 3 | 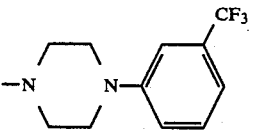 | 160–161 | $C_{20}H_{25}O_2N_6F$ | 59.95<br>59.60 | 6.31<br>6.27 | 20.99<br>21.17 |
| 27 | 3 | 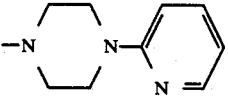 | 116–118 | $C_{21}H_{25}O_2N_6F_3$ | 55.98<br>55.88 | 5.60<br>5.63 | 18.66<br>18.68 |
| 28 | 3 | 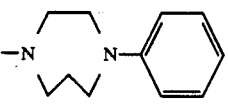 | 152–154 | $C_{19}H_{25}O_2N_7$ | 60.42<br>60.34 | 6.86<br>7.10 | 24.67<br>24.50 |
| 29 | 3 | 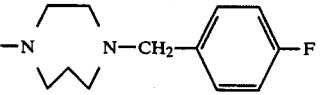 | 90–92 | $C_{21}H_{28}O_2N_6$ | 63.60<br>63.67 | 7.13<br>7.09 | 21.20<br>21.10 |
| 30 | 3 | 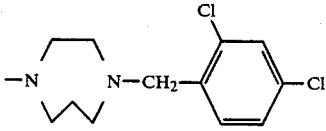 | 205–210 (dec.) | $C_{22}H_{29}O_2N_6F$<br>.2HCl | 52.69<br>52.63 | 6.24<br>6.19 | 16.75<br>16.64 |
| 31 | 3 |  | 250–255 (dec.) | $C_{22}H_{28}O_2N_6Cl_2$<br>.2HCl.H$_2$O | 47.83<br>47.61 | 5.48<br>5.30 | 15.22<br>15.17 |

TABLE 4-continued
| Example No. | n | Z | M.P. (°C) | Molecular formula | Elementary analysis upper column: Calculated lower column: Found | | |
|---|---|---|---|---|---|---|---|
| | | | | | C | H | N |
| 32 | 3 |  | 192–197 (dec.) | $C_{22}H_{29}O_2N_6Cl$ ·2HCl | 51.01 50.68 | 6.05 6.03 | 16.23 15.93 |
| 33 | 3 |  | 197–203 (dec.) | $C_{24}H_{34}O_4N_6$ ·2HCl·$C_2H_5OH$ | 52.97 52.68 | 7.20 7.48 | 14.26 14.18 |
| 34 | 3 |  | 262–270 (dec.) | $C_{21}H_{27}O_2N_5$ ·HCl | 60.34 59.91 | 6.77 6.55 | 16.76 17.03 |
| 35 | 3 |  | 152–154 | $C_{21}H_{27}O_3N_5$ | 63.44 63.67 | 6.86 7.07 | 17.62 17.68 |
| 36 | 3 |  | 148–150 | $C_{24}H_{33}O_2N_5$·HCl ·2$H_2O$ | 62.65 62.43 | 7.46 7.45 | 15.23 15.16 |
| 37 | 3 |  | 92–95 | $C_{17}H_{25}O_4N_5$ ·½$H_2O$ | 54.81 55.24 | 7.05 6.77 | 18.80 19.08 |
| 38 | 4 |  | 156–158 | $C_{21}H_{28}O_2N_6$ | 63.60 63.68 | 7.13 7.12 | 21.20 21.10 |
| 39 | 4 |  | 126–127 | $C_{22}H_{30}O_3N_6$ | 61.94 62.10 | 7.10 7.08 | 19.70 19.50 |
| 40 | 4 |  | 69–73 | $C_{22}H_{30}O_3N_6$ | 61.94 61.98 | 7.10 7.00 | 19.70 19.63 |
| 41 | 4 |  | 145–146 | $C_{22}H_{30}O_3N_6$ | 61.94 62.11 | 7.10 6.95 | 19.70 19.76 |

TABLE 4-continued
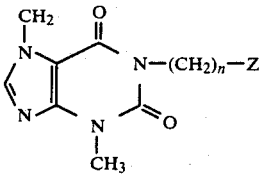
| Example No. | n | Z | M.P. (C) | Molecular formula | Elementary analysis upper column: Calculated lower column: Found | | |
|---|---|---|---|---|---|---|---|
| | | | | | C | H | N |
| 42 | 4 | 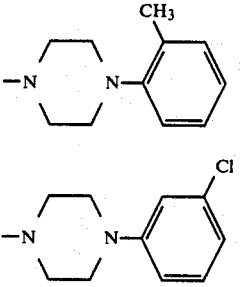 | 132-134 | $C_{22}H_{30}O_2N_6$ | 64.35<br>64.80 | 7.38<br>7.52 | 20.47<br>20.79 |
| 43 | 4 | 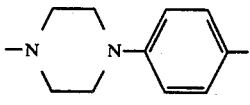 | 125 | $C_{21}H_{27}O_2N_6Cl$ | 58.52<br>58.24 | 6.33<br>6.31 | 19.53<br>19.51 |
| 44 | 4 | 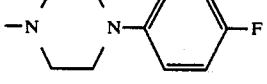 | 170-171 | $C_{21}H_{27}O_2N_6Cl$ | 58.52<br>58.67 | 6.33<br>6.23 | 19.53<br>19.55 |
| 45 | 4 | 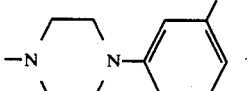 | 129-131 | $C_{21}H_{27}O_2N_6F$ | 60.84<br>60.82 | 6.58<br>6.52 | 20.28<br>20.19 |
| 46 | 4 | 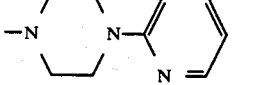 | 120-122 | $C_{22}H_{27}O_2N_6F_3$ | 56.88<br>56.84 | 5.87<br>5.84 | 18.09<br>18.01 |
| 47 | 4 | 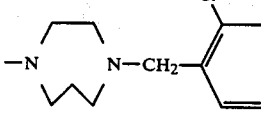 | 175-176 | $C_{20}H_{27}O_2N_7$ | 60.42<br>60.34 | 6.86<br>7.10 | 24.67<br>24.50 |
| 48 | 4 | 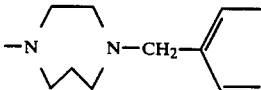 | 238-244 (dec.) | $C_{23}H_{31}O_2N_6Cl$ .2HCl | 51.93<br>51.51 | 6.27<br>6.38 | 15.80<br>15.53 |
| 49 | 4 | 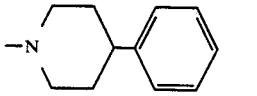 | 85-87 | $C_{23}H_{30}O_2N_6Cl_2$ | 55.97<br>55.83 | 6.14<br>5.86 | 17.03<br>16.87 |
| 50 | 4 | 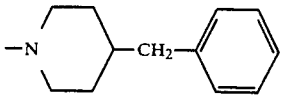 | 110-112 | $C_{22}H_{29}O_2N_5$ | 66.80<br>66.81 | 7.40<br>7.36 | 17.71<br>17.72 |
| 51 | 4 |  | 156-160 | $C_{23}H_{31}O_2N_5$ .HCl.2H$_2$O | 57.30<br>57.01 | 7.54<br>7.01 | 14.53<br>14.37 |

TABLE 4-continued
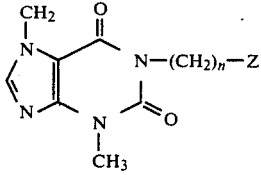
| Example No. | n | Z | M.P. (C) | Molecular formula | Elementary analysis upper column: Calculated lower column: Found | | |
|---|---|---|---|---|---|---|---|
| | | | | | C | H | N |
| 52 | 4 | 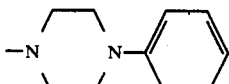 | 165–167 | $C_{25}H_{35}O_2N_5$ .HCl.H$_2$O | 61.01 60.70 | 7.80 7.66 | 14.23 13.82 |
| 53 | 5 | 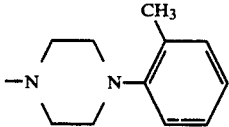 | 113–115 | $C_{22}H_{30}O_2N_6$ | 64.36 64.20 | 7.37 7.41 | 20.47 20.58 |
| 54 | 5 | 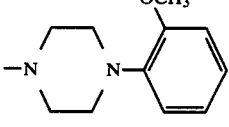 | 98–99 | $C_{23}H_{32}O_2N_6$ | 65.05 64.92 | 7.61 7.56 | 19.80 19.69 |
| 55 | 5 | 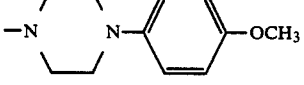 | 135–137 | $C_{23}H_{32}O_3N_6$ | 62.69 62.53 | 7.34 7.43 | 19.08 19.07 |
| 56 | 5 | 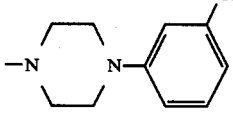 | 120–121 | $C_{23}H_{32}O_3N_6$ | 62.69 62.89 | 7.33 7.38 | 19.08 18.95 |
| 57 | 5 | 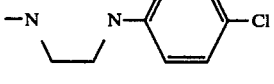 | 163–164 | $C_{22}H_{29}O_2N_6Cl$ | 59.37 59.55 | 6.58 6.57 | 18.89 18.73 |
| 58 | 5 | 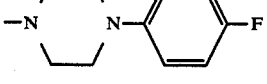 | 168–170 | $C_{22}H_{29}O_2N_6Cl$ | 59.37 59.48 | 6.58 6.52 | 18.89 18.85 |
| 59 | 5 | 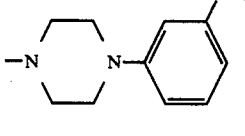 | 130–132 | $C_{22}H_{29}O_2N_6F$ | 61.65 61.56 | 6.83 6.79 | 19.61 19.73 |
| 60 | 5 | 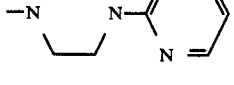 | 133–135 | $C_{23}H_{29}O_2N_6F_3$ | 57.72 57.63 | 6.12 6.16 | 17.56 17.53 |
| 61 | 5 |  | 98–100 | $C_{21}H_{29}O_2N_7$ | 61.28 61.39 | 7.12 7.25 | 23.83 23.75 |

TABLE 4-continued

Structure: 7-methyl-1-methyl-xanthine-8-carboxamide with N-(CH₂)ₙ-Z substituent

| Example No. | n | Z | M.P. (°C) | Molecular formula | Calculated C | Calculated H | Calculated N | Found C | Found H | Found N |
|---|---|---|---|---|---|---|---|---|---|---|
| 62 | 5 | -N(piperazinyl)-phenyl | 107–108 | $C_{23}H_{32}O_2N_6$ | 65.05 | 7.61 | 19.80 | 64.68 | 7.75 | 19.54 |
| 63 | 5 | -N(piperidinyl)-phenyl | 100–102 | $C_{23}H_{31}O_2N_5$ | 67.45 | 7.63 | 17.10 | 67.22 | 7.81 | 17.21 |
| 64 | 5 | -N(piperidinyl)-CH₂-phenyl | 141–143 | $C_{24}H_{33}O_2N_5 \cdot HCl \cdot 2H_2O$ | 58.10 | 7.73 | 14.12 | 58.18 | 7.29 | 14.45 |
| 65 | 5 | -N(piperidinyl)-(CH₂)₃-phenyl | 165 | $C_{26}H_{37}O_2N_6 \cdot HCl \cdot 2H_2O$ | 59.57 | 8.09 | 13.36 | 59.40 | 7.63 | 13.50 |
| 66 | 5 | -N(piperazinyl)-phenyl | 106–107 | $C_{23}H_{32}O_2N_6$ | 65.05 | 7.61 | 19.80 | 65.11 | 7.52 | 19.58 |
| 67 | 5 | -N(piperazinyl)-(2-OCH₃)phenyl | 108–109 | $C_{24}H_{34}O_3N_6$ | 63.40 | 7.55 | 18.49 | 63.14 | 7.34 | 18.37 |
| 68 | 6 | -N(piperazinyl)-(4-OCH₃)phenyl | 105–107 | $C_{24}H_{34}O_3N_6$ | 63.40 | 7.55 | 18.49 | 62.98 | 7.23 | 18.16 |
| 69 | 6 | -N(piperazinyl)-(4-Cl)phenyl | 159–160 | $C_{23}H_{31}O_2N_6Cl$ | 60.17 | 6.82 | 18.31 | 60.34 | 6.90 | 18.46 |
| 70 | 6 | -N(piperazinyl)-(4-F)phenyl | 135–136 | $C_{23}H_{31}O_2N_6F$ | 62.41 | 7.07 | 18.99 | 62.46 | 7.05 | 18.95 |
| 71 | 6 | -N(piperazinyl)-(3-CF₃)phenyl | 110–111 | $C_{24}H_{31}O_2N_6F_3$ | 58.51 | 6.36 | 17.06 | 58.45 | 6.32 | 17.10 |
| 72 | 6 | -N(piperazinyl)-(2-pyridyl) | 106–107 | $C_{22}H_{31}O_2N_7$ | 62.08 | 7.36 | 23.04 | 62.41 | 7.34 | 22.74 |

TABLE 4-continued
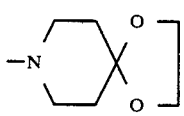
| Example No. | n | Z | M.P. (C) | Molecular formula | Elementary analysis upper column: Calculated lower column: Found | | |
|---|---|---|---|---|---|---|---|
| | | | | | C | H | N |
| 73 | 6 | 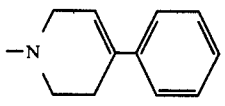 | 86–88 | $C_{20}H_{31}O_4N_5$ | 59.23<br>59.04 | 7.72<br>7.83 | 17.27<br>17.09 |
| 74 | 2 | 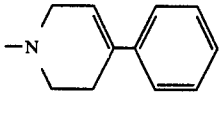 | 134–135 | $C_{20}H_{23}O_2N_5$ | 65.72<br>65.84 | 6.36<br>6.32 | 19.17<br>19.23 |
| 75 | 3 | 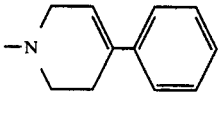 | 80–82 | $C_{21}H_{25}O_2N_5$ | 66.46<br>65.96 | 6.65<br>6.87 | 18.46<br>18.10 |
| 76 | 4 | 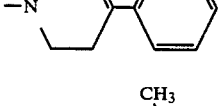 | 102–103 | $C_{22}H_{27}O_2N_5$ | 67.14<br>67.14 | 6.93<br>6.96 | 17.80<br>17.87 |
| 77 | 5 | 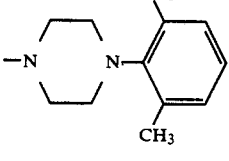 | 102–104 | $C_{23}H_{29}O_2N_5$ | 67.77<br>67.53 | 7.19<br>7.01 | 17.19<br>17.34 |
| 78 | 2 | 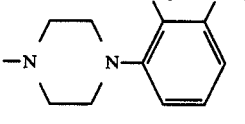 | 151–153 | $C_{21}H_{28}O_2N_6$ | 63.60<br>63.60 | 7.13<br>7.05 | 21.20<br>21.28 |
| 79 | 2 | 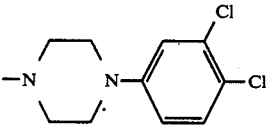 | 161–162 | $C_{21}H_{28}O_2N_6$ | 63.60<br>63.67 | 7.13<br>7.07 | 21.20<br>21.16 |
| 80 | 4 | 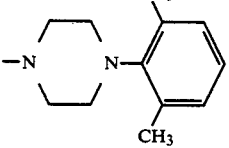 | 140–142 | $C_{21}H_{26}O_2N_6Cl_2$ | 54.19<br>54.24 | 5.64<br>5.71 | 18.06<br>17.91 |
| 81 | 5 |  | 121–123 | $C_{24}H_{34}O_2N_6$ | 65.71<br>65.68 | 7.38<br>7.73 | 19.16<br>19.36 |

TABLE 4-continued

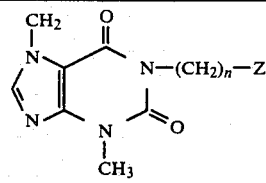

| Example No. | n | Z | M.P. (C) | Molecular formula | Elementary analysis upper column: Calculated lower column: Found | | |
|---|---|---|---|---|---|---|---|
| | | | | | C | H | N |
| 82 | 5 | 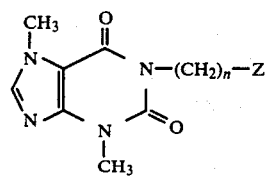 | 118–120 | $C_{24}H_{34}O_2N_6$ | 65.71<br>65.65 | 7.38<br>7.95 | 19.16<br>18.94 |

The embodiments of the invention in which an exclusive property or privilege is claimed are defined as follows:

1. A compound having the formula

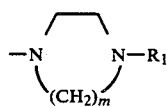

wherein Z is a member selected from the group consisting of

A. a group having the formula

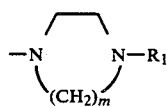

wherein m is the integer 2 or the integer 3, and $R_1$ is pyridyl or a group having the formula

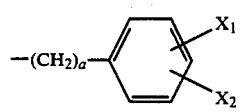

wherein $X_1$ and $X_2$, which can be the same or different, each is hydrogen, lower alkyl, lower alkoxy, trifluoromethyl or halogen, and a is an integer of 0 to 3;

B. a group having the formula

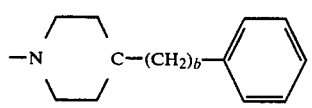

C. a group having the formula

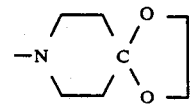

D. a group having the formula

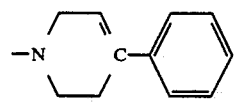

and E. a group having the formula

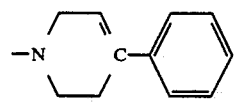

and n is an integer of 2 to 8, with the proviso that when Z is

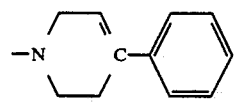

n is an integer of 3 to 8, and pharmaceutically acceptable acid addition salts thereof.

2. The compound as set forth in claim 1 having the formula

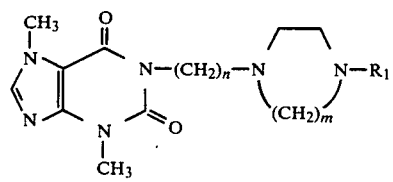

wherein m is the integer 2 or the integer 3 and $R_1$ is pyridyl or a group having the formula $$-(CH_2)_a-\text{\large\textcircled{}}\begin{smallmatrix}X_1\\X_2\end{smallmatrix}$$

wherein $X_1$ and $X_2$, which can be the same or different, each is hydrogen, lower alkyl, lower alkoxy, trifluoromethyl or halogen, and a is an integer of 0 to 3;

and n is an integer of 2 to 8, with the proviso that when m is 2 and $R_1$ is the group expressed by the formula $$\text{\large\textcircled{}}$$

n is an integer of 3 to 8.

3. The compound as set forth in claim 1 having the formula

[Structure: imidazole-CO-N-(CH_2)_2-N-piperazine-phenyl-OCH_3, with N-CH_3 groups]

4. The compound as set forth in claim 1 having the formula

[Structure: imidazole-CO-N-(CH_2)_3-N-piperazine-phenyl-OCH_3, with N-CH_3 groups]

5. The compound as set forth in claim 1 having the formula

[Structure: imidazole-CO-N-(CH_2)_5-N-piperazine-phenyl, with N-CH_3 groups]

6. The compound as set forth in claim 1 having the formula

[Structure: imidazole-CO-N-(CH_2)_6-N-piperazine-phenyl-OCH_3, with N-CH_3 groups]

7. The compound as set forth in claim 1 having the formula

[Structure: imidazole-CO-N-(CH_2)_4-N-piperazine-phenyl-CF_3, with N-CH_3 groups]

8. The compound as set forth in claim 1 having the formula

[Structure: imidazole-CO-N-(CH_2)_4-N-piperazine-phenyl-OCH_3, with N-CH_3 groups]

9. A pharmaceutical composition comprising a therapeutically effective amount of a compound as claimed in claim 1, for vasodilating purposes, in combination with a pharmacologically acceptable carrier.

10. A pharmaceutical composition comprising a therapeutically effective amount of a compound as claimed in claim 1, for tranquilizing purposes, in combination with a pharmacologically acceptable carrier.

11. A method for treating a subject suffering from blood circulatory insufficiency which comprises administering to the subject a pharmaceutical composition as claimed in claim 9.

12. A method for treating a subject suffering from psychotropic illness which comprises administering to the subject a pharmaceutical composition as claimed in claim 10.

13. A pharmaceutical composition comprising a therapeutically effective amount of a compound as claimed in claim 1, for analogesic purposes, in combination with a pharmacologically acceptable carrier.

14. A method for treating a subject suffering from a pain which comprises administering to the subject a pharmaceutical composition as claimed in claim 13.

15. The compound having the formula

[Structure: imidazole-CO-N-(CH_2)_n-N-piperazine-phenyl with $X_1$ and $X_2$ substituents, with N-CH_3 groups]

wherein $X_1$ and $X_2$, which are the same or different, each is hydrogen, lower alkyl, lower alkoxy, trifluoromethyl or halogen, and n is an integer of 2 to 8, with the proviso that when $X_1$ and $X_2$ are both hydrogen, n is an integer of 3 to 8, and pharmacologically acceptable acid addition salts thereof.

16. The compound as set forth in claim 15 having the formula

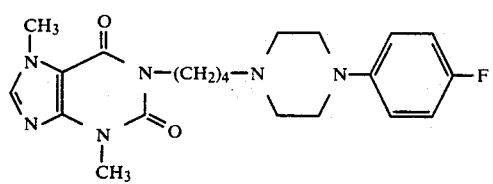
and pharmacologically acceptable acid addition salts thereof.
17. The compound as set forth in claim 15 having the formula
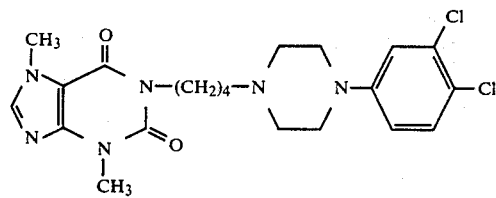
and pharmacologically acceptable acid addition salts thereof.
18. The compound as set forth in claim 1 or claim 15 wherein n is an integer of 4, 5 or 6.
* * * * *

UNITED STATES PATENT AND TRADEMARK OFFICE
CERTIFICATE OF CORRECTION

PATENT NO. : 4 493 837

DATED : January 15, 1985

INVENTOR(S) : Hachiro Sugimoto et al

It is certified that error appears in the above-identified patent and that said Letters Patent is hereby corrected as shown below:

Column 27, line 65; insert the following sentence:
---wherein b is an integer of 0 to 3;---.

Signed and Sealed this

Sixth Day of August 1985

[SEAL]

Attest:

DONALD J. QUIGG

Attesting Officer    Acting Commissioner of Patents and Trademarks